(12) United States Patent
Scott et al.

(10) Patent No.: US 6,505,069 B2
(45) Date of Patent: *Jan. 7, 2003

(54) ELECTROCHEMICALLY REACTIVE CATHODES FOR AN ELECTROTRANSPORT DEVICE

(75) Inventors: Erik R. Scott, Golden Valley, MN (US); Lothar W. Kleiner, Los Altos, CA (US)

(73) Assignee: ALZA Corporation, Mountain View, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/239,233

(22) Filed: Jan. 28, 1999

(65) Prior Publication Data

US 2002/0055704 A1 May 9, 2002

Related U.S. Application Data

(60) Provisional application No. 60/072,806, filed on Jan. 28, 1998, and provisional application No. 60/072,823, filed on Jan. 28, 1998.

(51) Int. Cl.[7] ................................................. A61N 1/30
(52) U.S. Cl. ........................ 604/20; 604/289; 607/152; 29/527.5; 29/527.7; 427/2.31; 427/125
(58) Field of Search ................................ 607/152, 153; 604/20, 21, 890.1, 289; 29/527.5, 527.7; 427/2.1, 2.31, 125, 96

(56) References Cited

U.S. PATENT DOCUMENTS

| 4,110,130 | A | * | 8/1978 | Nadkarni | .................... 419/38 |
| 4,383,529 | A | | 5/1983 | Webster | |
| 4,474,604 | A | * | 10/1984 | Nakamura et al. | .............. 264/8 |
| 4,747,819 | A | | 5/1988 | Phipps et al. | |
| 4,847,980 | A | * | 7/1989 | Witkowski et al. | .......... 264/104 |
| 5,147,297 | A | | 9/1992 | Myers et al. | |
| 5,405,317 | A | | 4/1995 | Myers et al. | |
| 5,427,736 | A | * | 6/1995 | Ritter et al. | ................... 419/48 |
| 5,533,971 | A | * | 7/1996 | Phipps | |
| 5,543,098 | A | * | 8/1996 | Myers et al. | |
| 5,573,503 | A | | 11/1996 | Untereker et al. | |
| 5,622,530 | A | * | 4/1997 | Phipps | |
| 5,911,919 | A | * | 6/1999 | Billings | ...................... 252/515 |
| 6,190,579 | B1 | * | 2/2001 | Billings | ...................... 252/515 |

FOREIGN PATENT DOCUMENTS

| EP | 0 498 353 A2 | 8/1992 |
| EP | 0 774 272 A1 | 5/1997 |
| WO | WO 96/09851 | 4/1996 |

* cited by examiner

Primary Examiner—Brian L. Casler
Assistant Examiner—Jeremy Thissell
(74) Attorney, Agent, or Firm—Owen Bates

(57) ABSTRACT

The present invention relates generally to improved cathodes (24) for use in an electrotransport device (10) for transdermally or transmucosally delivering a beneficial agent (e.g., a drug) to, or extracting a body analyte (e.g., glucose) from, the body surface of a patient. Most particularly, the present invention relates to a cathodic electrode (24) in the form of a silver halide foil which can be made, e.g., by forging particulate silver chloride. The cathode (24) does not absorb agent (e.g., drug), eliminates the need for binders, solvents and processing aids during the manufacturing process, and increases dimensional freedom of design.

15 Claims, 2 Drawing Sheets

ELECTROCHEMICALLY REACTIVE CATHODES FOR AN ELECTROTRANSPORT DEVICE

This application claims the benefit of Provisional application Ser. No. 60/072,806, filed Jan. 28, 1998, and Provisional application Ser. No. 60/072,823 filed Jan. 28, 1998.

TECHNICAL FIELD

The present invention relates generally to improved cathodes for use in an electrotransport device for delivering a beneficial agent (e.g., a drug), or for sampling an agent (e.g., a body analyte such as glucose) through a body surface of a patient. More particularly, the present invention relates to electrochemically reactive cathodes for an electrotransport device.

BACKGROUND ART

The term "electrotransport" refers generally to the delivery or extraction of an agent (charged, uncharged, or mixtures thereof through a body surface (such as skin, mucous membrane, or nails) wherein the delivery or extraction is at least partially electrically induced or aided by the application of an electric potential. The electrotransport process has been found to be useful in the transdermal administration of many drugs including lidocaine, hydrocortisone, fluoride, penicillin, and dexamethasone. A common use of electrotransport is in diagnosing cystic fibrosis by delivering pilocarpine iontophoretically. The pilocarpine stimulates production of sweat. The sweat is then collected and analyzed for its chloride content to detect the presence of the disease.

Electrotransport devices generally employ two electrodes, positioned in intimate contact with some portion of the animal's body (e.g., the skin). A first electrode, called the active or donor electrode, delivers the therapeutic agent (e.g., a drug) into the body. The second electrode, called the counter or return electrode, closes an electrical circuit with the first electrode through the animal's body. A source of electrical energy, such as a battery, supplies electric current to the body through the electrodes. For example, if the therapeutic agent to be delivered into the body is positively charged (i.e., cationic), the anode is the active electrode and the cathode is the counter electrode to complete the circuit. If the therapeutic agent to be delivered is negatively charged (i.e., anionic), the cathode is the donor electrode and the anode is the counter electrode.

A widely used electrotransport process, electromigration (also called iontophoresis), involves the electrically induced transport of charged ions (e.g., drug ions) through a body surface. Another type of electrotransport, called electroosmosis, involves the trans-body surface (e.g., transdermal) flow of a liquid under the influence of the applied electric field. Still another type of electrotransport process, called electroporation, involves forming transiently existing pores in a biological membrane by applying high voltage pulses. In any given electrotransport system, one or more of these processes may occur simultaneously to some extent.

Most transdermal electrotransport devices have an anodic and a cathodic electrode assembly, each electrode assembly being comprised of an electrically conductive electrode in ion-transmitting relation with an ionically conductive liquid reservoir which in use is placed in contact with the patient's skin. Gel reservoirs such as those described in Webster U.S. Pat. 4,383,529 are the preferred form of reservoir since hydrated gels are easier to handle and manufacture than liquid-filled containers. Water is by far the preferred liquid solvent used in such reservoirs, in part because many drug salts are watersoluble and in part because water has excellent biocompatability, making prolonged contact between the hydrogel reservoir and the skin acceptable from an irritation standpoint.

The electrodes used in transdermal electrotransport devices are generally of two types; those that are made from materials that are not electrochemically reactive and those that are made from materials that are electrochemically reactive. Electrochemically non-reactive electrodes, such as stainless steel, platinum, and carbon-based electrodes, tend to promote electrochemical oxidation or reduction of the liquid solvent at the electrode/reservoir interface. When the solvent is water, the oxidation reaction (at the anodic electrode interface) produces hydronium ions, while the reduction reaction (at the cathodic interface) produces hydroxyl ions. Thus, one serious disadvantage with the use of electrochemically non-reactive electrodes is that pH changes occur during device operation due to the water oxidation and reduction reactions which occur at the electrode/reservoir interfaces. Oxidation and reduction of water can largely be avoided by using electrochemically reactive electrodes, as discussed in Phipps et al. U.S. Pat. Nos. 4,747,819 and 5,573,503. Preferred electrochemically oxidizable materials for use in the anodic electrode include metals such as silver, copper and zinc. Of these, silver is most preferred as it has better biocompatability compared to most other metals. Preferred electrochemically reducible materials for use in the cathodic electrode include metal halides. Of these, silver halides such as silver chloride are most preferred. While these electrode materials provide an elegant solution to the problem of pH drift in the electrotransport reservoirs, they have their own set of problems.

The silver halide cathodes produce only halide (e.g., chloride) anions when they are electrochemically reduced $(AgX \rightarrow Ag + X^-)$ which anions are naturally present in the body in significant quantities. Thus, delivery of the chloride ions from the cathode into the patient creates no biocompatability problems. While the silver halide cathodes are quite biocompatible, they have serious disadvantages.

These disadvantages stem in part from the methods used to make the prior art silver halide cathodes. Generally, the prior art silver halide cathodes are made by one of several methods. In two of these methods, a silver foil is either reacted electrolytically with hydrochloric acid or dipped in molten silver chloride in order to form a silver chloride coating on the foil. Such coatings tend to have a limited thickness, thereby limiting the electrochemical capacity of such cathodes. Furthermore, coatings formed in either of these manners are prone to flaking off when the silver foil is flexed. A further disadvantage in connection with the electrolytic reaction of silver foil with hydrochloric acid is that it is a very slow process and not easily amenable to commercial manufacturing.

The third method of making prior art silver halide cathodes involves mixing silver halide particles into a binder, such as a polymeric matrix. This technique is described in Myers et al. U.S. Pat. Nos. 5,147,297 and 5,405,317. Because the polymeric binder is an electrically insulating material, these composite film electrodes also preferably have electrically conductive fillers such as carbon or metal particles, flakes or fibers. Typically, such composite cathodes comprise at least 20 vol. %, and more typically at least 40 vol. % of the inert polymeric binder. The polymeric binder and the conductive filler can create several problems in electrotransport drug delivery devices. For example, polymeric binders have a tendency to absorb drug (and/or other non-agent excipients in the electrolyte reservoir formulation such as anti-microbial agents) from the immediately adjacent electrolyte (i.e., donor or counter) reservoir. In some applications, binders in the donor electrode can absorb up to 50% of the agent in the donor reservoir. Such absorption is problematic because the absorbed agent is not delivered through the body surface causing insufficient therapy or the need to excessively load the reservoir with agent to compensate for such absorption. This means that excess drug and/or excipients may have to be loaded into the reservoir in order to compensate for the drug absorption by the electrode binder. This increases the total drug/excipient loading in the system and makes such systems more expensive, particularly with high cost drugs. Secondly, when the conductive filler is carbon or graphite, such materials have a very high affinity to organic compounds and thus there is a strong tendency for the drug in the adjacent drug reservoir to be adsorbed onto the surface of the conductive filler.

In addition, composite electrodes having more than 20 vol. % binder and typically more than 40 vol. % binder, are necessarily thicker and have lower discharge capacity, due to the inert nature of the binder. Electrode thickness is of particular concern since in recent years, electrotransport delivery devices have become much smaller, particularly with the development of miniaturized electrical circuits (e.g., integrated circuits) and more powerful lightweight batteries (e.g., lithium batteries). Added thickness is also undesirable because it takes away from other dimensional freedoms for system design, such as employing larger reservoirs, higher capacity thick batteries, more advanced and thicker electronic circuitry, biofeedback components, LCD displays, and other electronic components.

Another disadvantage with composite electrodes is that undesirable compounds can leach from the composite electrode into the adjacent drug or electrolyte reservoir and, possibly, onto or through the body surface. Such undesirable compounds may include impurities, residual solvent, unreacted monomer, dissolved binder, and the like. As a result, the presence of such compounds may deleteriously affect the biocompatability, efficacy and safety of the prior art electrotransport devices.

Still another disadvantage of the composite electrode is that hazardous materials (e.g., solvents) may be discharged into the environment when the electrode is manufactured. For example, silver chloride inks can be made by blending particulate silver chloride with polyisobutylene dissolved in a volatile organic solvent. The mixture is generally sprayed or roll coated onto a substrate and dried. Unless the overspray is filtered, scrubbed and burned, it is emitted into the atmosphere. Moreover, solvent is given off as the ink dries, which is difficult and expensive to capture. Thus, the environmentally hazardous materials used to process ink based and other polymeric electrodes are costly to recover.

Hence, there is a need for an improved electrode comprised of a reducible silver halide (such as silver chloride) to replace silver halide-coated silver foil electrodes and polymeric composite electrodes containing silver chloride particles, and to overcome the associated disadvantages thereof. There is also a need for an electrochemically reactive cathodic electrode having improved mechanical properties and cathodic discharge performance.

DESCRIPTION OF THE INVENTION

The present invention provides a cathodic electrode assembly for an electrotransport device adapted to deliver a therapeutic agent (e.g., a drug), or extract a body analyte (e.g., glucose) through a body surface such as skin. The cathodic electrode assembly includes a solid silver halide cathodic electrode. The cathodic electrode assembly also includes a cathodic electrolyte reservoir which is positioned adjacent and in ion-transmitting relation with the cathode. In use, the cathodic electrolyte reservoir is positioned intermediate the cathode and the body surface, and in ion-transmitting relation with the body surface.

The cathodic electrode is comprised of at least 95 vol. % silver halide, and preferably is comprised of substantially 100% silver halide. The cathode has an organic material content of less than 1 vol. % and preferably is substantially free of any organic materials such as binders, adhesives or other polymers. The cathodic electrode is also substantially free of any electrically conductive filler which can absorb materials contained in the electrolyte reservoir. A particularly preferred form of the silver halide cathodic electrode is substantially pure silver chloride foil having a thickness of 0.05 to 0.15 mm. In cases where the cathodic electrode is substantially pure silver chloride, the electrode preferably has an electrically conductive current collector positioned against a surface thereof.

The present invention also provides a method of making a cathodic electrode assembly for such an electrotransport delivery/sampling device. The method includes forming a solid silver halide cathodic electrode comprised of at least 95 vol. % silver halide and containing less than 1 vol. % organic materials and being substantially free of any electrically conductive filler which absorbs materials from the cathodic electrolyte reservoir. The electrode is then positioned against an electrolyte reservoir to form the electrode assembly. The electrode forming step can be performed by any number of techniques including (1) forging silver halide particles; (2) casting molten silver halide to form a sheet and then calendering the sheet to form a foil; (3) depositing a slurry of silver halide particles onto a screen, drawing off the liquid to form a silver halide sheet and calendering the sheet to form a foil; and (4) mixing silver halide particles in an organic binder, forming the mix into a sheet and then pyrolyzing the sheet to burn off the organic binder.

The present invention overcomes the disadvantages associated with composite electrodes and the prior silver chloride electrode layers. The electrodes of the present invention do not have the disadvantages associated with composite silver chloride electrodes, such as drug and/or excipient absorption, introduction of contaminants, unnecessarily great thickness, and solvent emission during the manufacturing process.

DEFINITIONS

Figure 1:
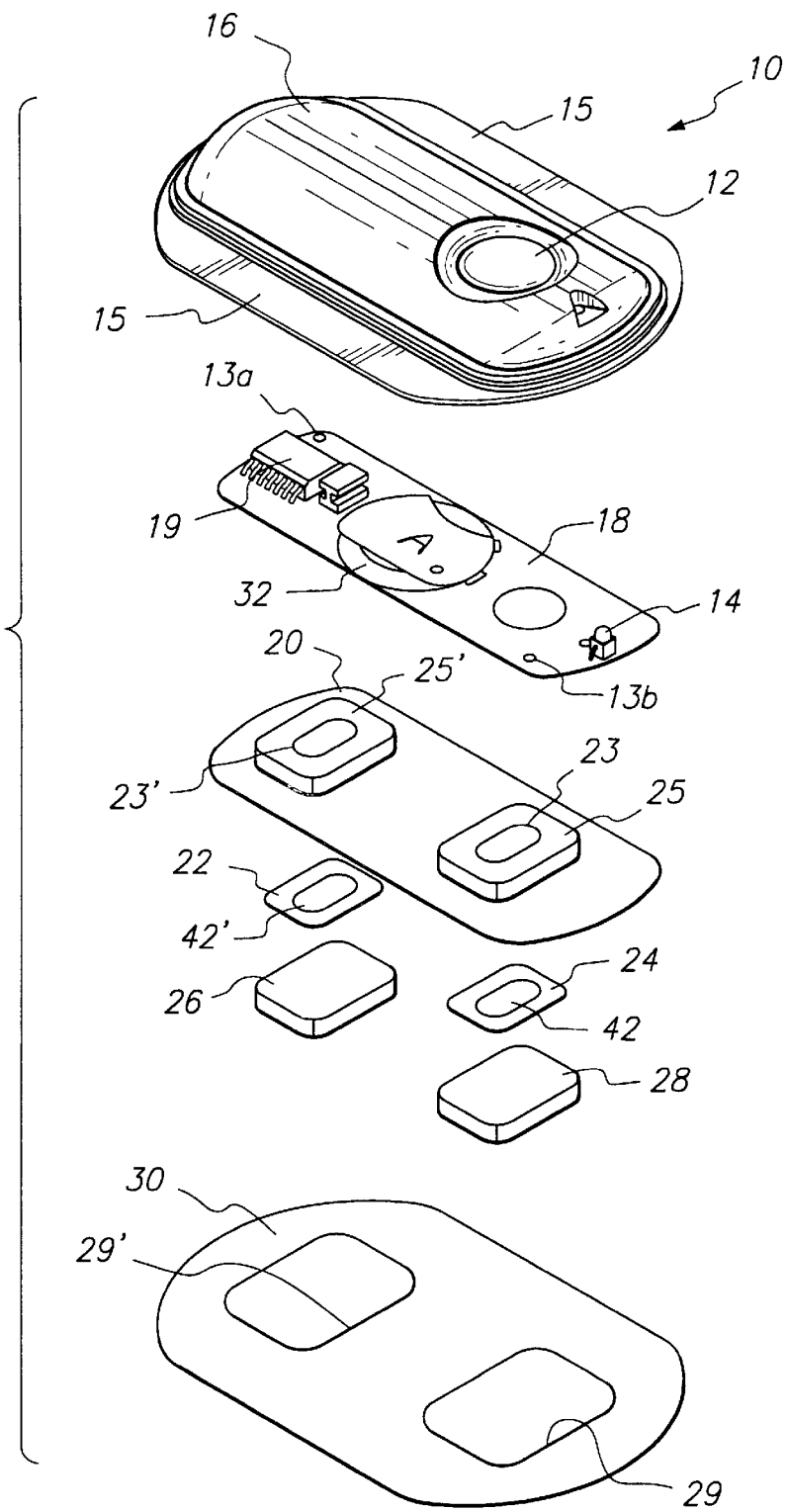
FIG. 1 is a perspective exploded view of an electrotransport device which can be used with the present invention.

As used herein, the term "cathodic electrode assembly" includes a collection of at least a cathodic electrode and a cathodic electrolyte reservoir used in an electrotransport device.

As used herein, the terms "cathode" and "cathodic electrode" are used interchangeably to mean the electrode of an electrotransport device which is electrically connected to the negative pole of the device power source.

As used herein, the term "electrical sheet resistance" means the surface resistance between opposite edges of a unit square of a material. Electrical sheet resistance (also sometimes called surface resistivity in the literature) is generally designated in the literature by the symbol $\rho_s$ and is used to characterize current flow over a surface. The resistance across a square is independent of the size of the square and the unit of sheet resistance is the ohm, or more superfluously (and as used herein), ohm/square. Since a conducting surface is always a layer with a finite thickness, t, the sheet resistance is related to the volume resistivity, $\rho_v$, of the layer by the following equation: $\rho_s = \rho_v \div t$. The sheet resistance of any given electrode or current conductor can be measured in accordance with the methods described in The American Society for Testing and Materials (ASTM), West Conshohoken, Pa., volume 10.02, Test Standard Designation D 4496-87 (reapproved 1993), entitled "Standard Test Method for D-C Resistance or Conductance of Moderately Conductive Materials", the disclosures of which are incorporated herein by reference.

As used herein, the term "body surface" includes the skin, mucosal membranes and/or nails of a living animal. In particular, it includes the skin of living humans.

As used herein, the term "electrolyte reservoir" means a liquid which contains, or which receives during device operation, dissolved ions. The term includes saline solutions used in counter cathodic electrodes and drug solutions or suspensions in cathodic donor electrodes. The term also includes matrices such as a sponge, fabric, or a polymer such as a gel which contains such a solution or suspension. The term includes both aqueous and non-aqueous solutions (e.g., solutions of dissolved electrolyte in a glycol or glycerol).

As used herein, the term "electrolyte reservoir formulation material(s)" means any material which is contained in the electrolyte reservoir.

As used herein, the term "organic materials" means any hydrocarboncontaining material, for example, binders, adhesives or other polymers.

As used herein, the term "volumetric discharge capacity" means the amount of charge that can be passed between the silver halide cathode and the cathodic electrolyte reservoir during electrochemical reduction of the silver halide per unit volume of the cathode. Volumetric discharge capacity has the units milliampere-hours per cubic centimeter of the electrode (mAhr/cm$^3$).

MODE FOR CARRYING OUT THE INVENTION

The present invention provides a silver halide electrode having a particular composition as a cathodic electrode in an electrotransport delivery or sampling device. As with conventional cathodic electrode assemblies, the cathodic electrode assembly of the present invention comprises a cathodic electrode positioned in ion-transmitting relation with a cathodic electrolyte reservoir. The electrolyte reservoir, in use, is adapted to be placed in iontransmitting relation with the body surface (e.g., skin) through which the agent is to be delivered or extracted. The silver halide electrode of the present invention can be used, in connection with therapeutic agent delivery, as either a donor electrode (e.g., for delivering an anionic therapeutic agent) or as a counter electrode (in which case the agent is delivered from a donor reservoir in the anodic electrode assembly). When the cathodic electrode of the present invention is used as a donor electrode, the cathodic electrolyte reservoir will contain the therapeutic agent to be delivered. When used as a counter electrode, the cathodic electrolyte reservoir will contain a biocompatible electrolyte, such as saline.

The silver halide cathode of the present invention is solid and is comprised of at least 95 vol. % silver halide. The high volume loading of silver halide gives the cathodic electrode of the present invention a very high volumetric discharge capacity. A further advantage of the most preferred substantially pure (i.e., 100% silver halide loading) silver halide electrodes of the present invention is that it is easier and less expensive to recover unused silver halide raw material left over from the manufacturing process since the silver halide does not need to be separated and recovered from polymeric binders.

The cathodic electrode of the present invention contains less than 1 vol. % organic materials and preferably is substantially free of any organic materials. The cathodic electrode is also substantially free of any electrically conductive filler such as carbon and graphite which can absorb or adsorb significant amounts of drug and/or other excipients from the adjacent cathodic electrolyte reservoir. One allowable exception to the foil being substantially free of electrically conductive fillers is metallic silver. Metallic silver can be present in the silver halide electrodes of the present invention in order to improve their electrical conductivity. Metallic silver is permitted since silver has substantially no tendency to adsorb drug and/or other excipients from the adjacent cathodic reservoir. The metallic silver should be homogeneously dispersed in the cathodic electrode and should be present in an amount of no more than about about 5 vol. % of the electrode.

A particularly preferred form of the silver halide electrode of the present invention is a sheet or foil having an aspect ratio, measured as the ratio of the longest length (l) of the sheet or foil to the thickness (t) of the sheet or foil, of at least 5 and preferably at least 10. Most preferably, the sheets/foils have a thickness of no more than about 0.5 mm and preferably less than about 0.25 mm. The silver halide foils are both flexible and ductile so that the foils can be calendered to achieve the necessary thickness for use in any given electrotransport device. Furthermore, the silver halide foils are non-friable, that is they do not flake or crumble which was a tendency of the prior art silver chloride-coated metal foil cathodes. One commercial source of substantially pure silver chloride, sold in the form of a strip having a thickness of 0.05 mm (0.002 inch), is made by Engelhard-CLAL of Carteret, N.J.

The silver halide cathode of the present invention can be made from silver halides such as silver chloride, silver bromide, silver iodide and silver fluoride. Of these, silver chloride is most preferred.

Because the silver halide electrodes of the present invention have such a high ($\geq 95$ vol. %) silver halide content, the electrodes inherently have a high volumetric discharge capacity. Typically, the silver halide electrodes of the present invention have a volumetric discharge capacity of at least about 500 mAhr/cm$^3$ and more preferably at least about 900 mAhr/cm$^3$. Thus, the silver foil cathodes of the present invention offer higher volumetric discharge capacities than composite cathodes containing high amounts (e.g., more than 40 vol. %) of inert binder materials.

The most preferred silver halide foil cathodes of the present invention generally have a thickness of less than 0.5 mm, and preferably from about 0.05 to 0.2 mm. Even with such thin foils, the silver halide foil cathodes have high volumetric discharge capacities due to their high silver halide content. The preferred silver halide foils can be made by a number of different methods as the invention is not limited thereby. For example, the foils can be made by forging in which particulate silver halide is compressed under high pressure (e.g., more than 1000 kg/cm$^2$) to form thin flexible sheets. Another technique that can be use to make a silver halide foil is to deposit a slurry of silver halide particles onto a screen, draw off the liquid and then calendering the resulting silver halide sheet. Still another method of making the silver halide foils is to cast molten silver halide (silver chloride has a melting temperature of 455° C.) into a sheet and then calendering the sheet to achieve the desired thickness.

FIG. 1 shows an exemplary electrotransport delivery device which can be used with the silver chloride foil cathode of the present invention. Device 10 comprises an upper housing 16 containing a circuit board assembly 18 a lower housing 20, electrodes 22 and 24, electrolyte gel reservoirs 26 and 28, and skin-compatible adhesive 30. Upper housing 16 has lateral wings 15, which assist in holding device 10 on a patient's skin. Upper housing 16 is preferably composed of an injection moldable elastomer (e.g., ethylene vinyl acetate). Printed circuit board assembly 18 comprises one or more electrical components 19 (e.g., an integrated circuit) and battery 32. Circuit board assembly 18 is attached to housing 16 by posts (not shown in FIG. 1) passing through openings 13a and 13b, the ends of the posts being heated/melted in order to heat stake the circuit board assembly 18 to the housing 16. Lower housing 20 is attached to the upper housing 16 by means of adhesive 30, the skin distal side of adhesive 30 being adhered to both lower housing 20 and upper housing 16 including the bottom surfaces of wings 15.

The outputs (not shown in FIG. 1) of the circuit board assembly 18 make electrical contact with cathodic electrode 24 (i.e., the silver halide cathode of the present invention) and anodic electrode 22 through current collectors 42 and 42', respectively. Current collectors 42 and 42' are composed of an electrically conductive adhesive which adheres to the skin distal sides of electrodes 24 and 22, respectively. The skin distal sides of current collectors 42 and 42' adhere to the circuit outputs (not shown) on the underside of circuit board assembly 18 through openings 23', 23 in the depressions 25', 25 formed in lower housing 20. Electrodes 22 and 24, in turn, are in direct mechanical and electrical contact with the skin-distal sides of electrolyte gel reservoirs 26 and 28. The skin-proximal sides of electrolyte gel reservoirs 26, 28 contact the patient's skin through the openings 29', 29 in adhesive 30.

Figure 2:
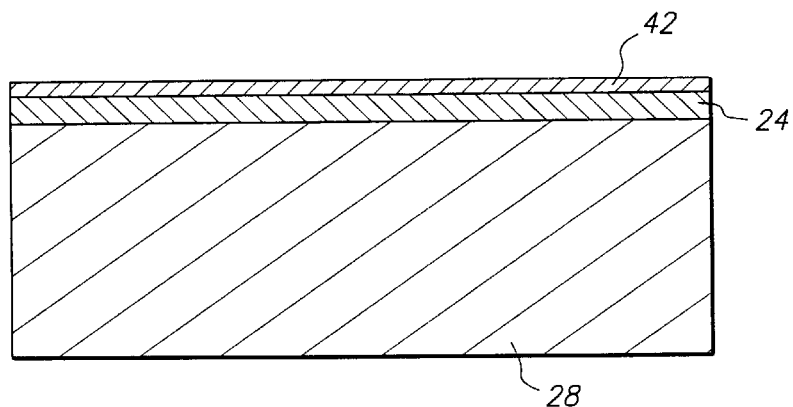
FIG. 2 is a preferred structure for a cathodic electrode assembly of the present invention.

As shown in FIG. 1, the silver halide cathode 24 of the present invention is preferably a thin layer which has one face which contacts an electrically conductive current collector 42, also preferably in the form of a thin sheet or layer. Most preferably, the current collector 42 contacts substantially all of the skin distal surface of cathode 24 as best shown in FIG. 2. The current collector is a highly conductive material such as a metal foil, an adhesive sheet loaded with electrically conductive filler such as carbon or metal particles or fibers, or a conductive ink or coating deposited on a surface of the cathode 24 or deposited on a substrate that is placed against the cathode 24.

Device 10 optionally has a feature which allows the patient to selfadminister a dose of drug by electrotransport. Upon depression of push button switch 12, the electronic circuitry on circuit board assembly 18 delivers a predetermined DC current to the electrodes/electrolyte reservoirs 42', 42 and 26, 28 for a delivery interval of predetermined length. The push button switch 12 is conveniently located on the topside of device 10 and is easily actuated through clothing. A double press of the push button switch 12 within a short time period, e.g., three seconds, is preferably used to activate the device for delivery of drug, thereby minimizing the likelihood of inadvertent actuation of the device 10. Preferably, the device transmits to the user a visual and/or audible confirmation of the onset of the drug delivery interval by means of LED 14 becoming lit and/or an audible signal from, e.g., a "beeper". Drug is delivered through the patient's skin by electrotransport, e.g., on the arm, over the predetermined delivery interval.

The push button switch 12, the electronic circuitry on circuit board assembly 18 and the battery 32 are adhesively "sealed" between upper housing 16 and lower housing 20. Upper housing 16 is preferably composed of a thermoplastic elastomeric material. Lower housing 20 is preferably composed of a plastic or elastomeric sheet material (e.g., polyethylene or polyethylene terephthalate copolymer) which can be easily molded to form depressions 25, 25' and cut to form openings 23, 23'. The assembled device 10 is preferably water-resistant (i.e., splash proof) and is most preferably waterproof. The system has a low profile that easily conforms to the body, thereby allowing freedom of movement at, and around, the wearing site. The electrolyte gel reservoirs 26 and 28 are located on the skin-contacting side of the device 10 and are sufficiently separated to prevent accidental electrical shorting during normal handling and use.

The device 10 adheres to the patient's body surface (e.g., skin) by means of a peripheral (i.e., surrounding the periphery of electrolyte gel reservoirs 26 and 28) adhesive 30. The adhesive 30 has adhesive properties which assures that the device 10 remains in place on the body during normal user activity, and yet permits reasonable removal after the predetermined (e.g., 24-hour) wear period.

The electrolyte gel reservoirs 26 and 28 each comprises liquid electrolyte contained in a gel matrix. When device 10 delivers a therapeutic agent, at least one of the gel reservoirs 26 and 28 contains a drug solution or suspension. Drug concentrations in the range of approximately $1 \times 10^{-4}$ M to 1.0 M or more can be used, with drug concentrations in the lower portion of the range being preferred. Suitable polymers for the gel matrix may comprise essentially any nonionic synthetic and/or naturally occurring polymeric materials. A polar nature is preferred when the active agent is polar and/or capable of ionization, so as to enhance agent solubility. Optionally, the gel matrix will be water swellable. Examples of suitable synthetic polymers include, but are not limited to, poly(acrylamide), poly(2-hydroxyethyl acrylate), poly(2-hydroxypropyl acrylate), poly(N-vinyl-2-pyrrolidone), poly(n-methylol acrylamide), poly(diacetone acrylamide), poly(2-hydroxylethyl methacrylate), poly(vinyl alcohol) and poly(allyl alcohol). Hydroxyl functional condensation polymers (i.e., polyesters, polycarbonates, polyurethanes) are also examples of suitable polar synthetic polymers. Polar naturally occurring polymers (or derivatives thereof suitable for use as the gel matrix are exemplified by cellulose ethers, methyl cellulose ethers, cellulose and hydroxylated cellulose, methyl cellulose and hydroxylkated methyl cellulose, gums such as guar, locust, karaya, xanthan, gelatin, and derivatives thereof. Ionic polymers can also be used for the matrix provided that the available counterions are either drug ions or other ions that are oppositely charged relative to the active agent.

As used herein, the term "agent" includes both agents which are sampled from the body, e.g., for diagnostic purposes, as well as, therapeutic agents which are delivered from the device into the body in order to achieve a therapeutic effect. In the context of sampling agents for diagnostic purposes, the agent can be any body analyte including electrolytes or glucose which are sampled in order to perform a diagnostic test such as measurement of blood glucose. In the context of therapeutic agent delivery, the term "agent" is used interchangeably with "drug", and each are intended to be given its broadest reasonable interpretation in the art as any therapeutically active substance which when delivered to a living organism produces a desired, usually beneficial, effect. For example, "agent" includes therapeutic compounds and molecules from all therapeutic categories including, but not limited to, anti-infectives (such as antibiotics and antivirals), analgesics (such as fentanyl, sufentanil, buprenorphine, and analgesic combinations), anesthetics, antiarthritics, antiasthmatics (such as terbutaline), anticonvulsants, antidepressants, antidiabetics, antidiarrheals, antihistamines, anti-inflammatories, antimigranes, antimotion sickness preparations (such as scopolamine and ondansetron), antineoplastics, antiparkinsonisms, antipruritics, antipsychotics, antipyretics, antispasmodics (including gastrointestinal and urinary), anticholinergics, sympathomimetrics, xanthine and derivatives thereof, cardiovascular preparations (including calcium channel blockers such as nifedipine, beta-agonists (such as dobutamine and ritodrine), beta blockers, antiarrythmics, antihypertensives (such as atenolol), ACE inhibitors (such as lisinopril), diuretics, vasodilators (including general, coronary, peripheral and cerebral), central nervous system stimulants, cough and cold preparations, decongestants, diagnostics, hormones (such as parathyroid hormones), hypnotics, immunosuppressives, muscle relaxants, parasympatholytics, parasympathomimetrics, prostaglandins, proteins, peptides, psychostimulants, sedatives and tranquilizers.

The electrotransport device of the present invention may also deliver drugs and/or agents including baclofen, beclomethasone, betamethasone, buspirone, cromolyn sodium, diltiazem, doxazosin, droperidol, encainide, fentanyl, hydrocortisone, indomethacin, ketoprofen, lidocaine, methotrexate, metoclopramide, miconazole, midazolam, nicardipine, piroxicam, prazosin, scopolamine, sufentanil, terbutaline, testosterone, tetracaine and verapamil.

The electrotransport device of the present invention may also deliver peptides, polypeptides, proteins and other macromolecules. Such molecules are known in the art to be difficult to deliver transdermally or transmucosally due to their size. For example, such molecules may have molecular weights in the range of 300–40,000 daltons and include, but not limited to, LHRH and analogs thereof (such as buserelin, gosserelin, gonadorelin, naphrelin and leuprolide), GHRH, GHRF, insulin, insulinotropin, heparin, calcitonin, octreotide, endorphin, TRH, NT-36 or N-[[(s)-4-oxo-2-azetidinyl]carbonyl]L-histidyl-L-prolinamide], liprecin, pituitary hormones (such as HGH, HMG, HCG, desmopressin acetate), follicile luteoids, a-ANF, growth factor releasing factor (GFRF), b-MSH, somatostatin, bradykinin, somatotropin, platelet-derived growth factor, asparaginase, bleomycin sulfate, chymopapain, cholecystokinin, chorionic gonadotropin, corticotropin (ACTH), erythropoietin, epoprostenol (platelet aggregation inhibitor), glucagon, hirulog, hyaluronidase, interferon, interleukin-2, menotropins (such as urofollitropin (FSH) and LH), oxytocin, streptokinase, tissue plasminogen activator, urokinase, vasopressin, desmopressin, ACTH analogs, ANP, ANP clearance inhibitors, angiotensin II antagonists, antidiuretic hormone agonists, antidiuretic hormone antagonists, bradykinin antagonists, CD4, ceredase, CSF's, enkephalins, FAB fragments, IgE peptide suppressors, IGF-1, neurotrophic factors, colony stimulating factors, parathyroid hormone and agonists, parathyroid hormone antagonists, prostaglandin antagonists, pentigetide, protein C, protein S, renin inhibitors, thymosin alpha-1 antitrypsin (recombinant), and TGF-beta.

While the invention has been described in conjunction with the preferred specific embodiments thereof, it is to be understood that the foregoing description as well as the examples which follow are intended to illustrate and not limit the scope of the invention. Other aspects, advantages and modifications within the scope of the invention will be apparent to those skilled in the art.

COMPARATIVE EXAMPLE

Figure 3:
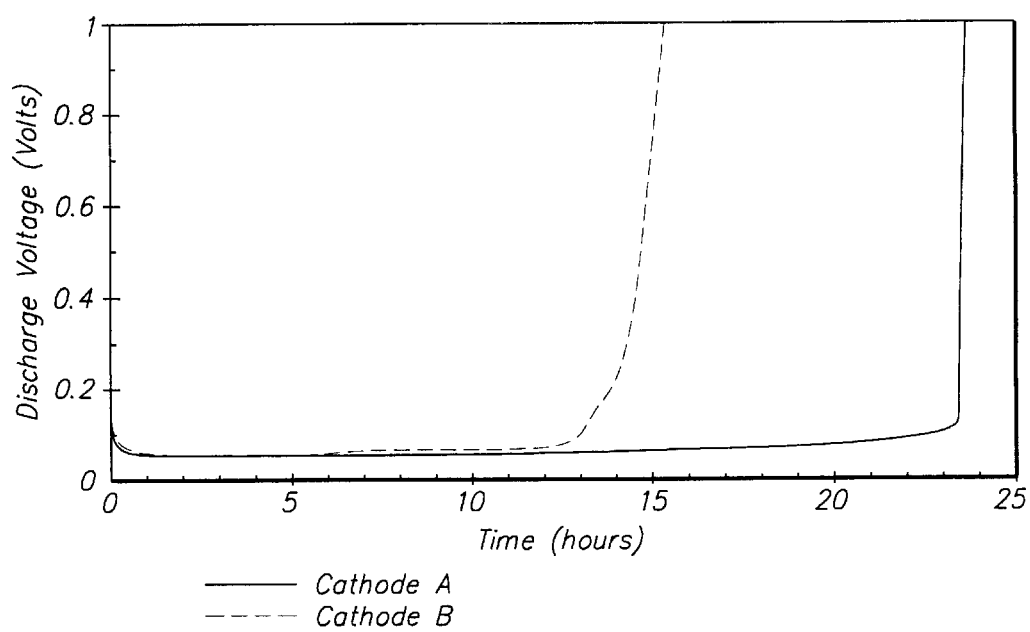
FIG. 3 is a graph illustrating the discharge characteristics of a silver chloride foil cathode of the present invention compared to a composite silver chloride loaded film cathode of the prior art.

A silver chloride foil cathode (Cathode A) was made by forging AgCl pellets having an approximate pellet thickness of about 0.05 to 0.4 mm (2 to 16 mil). The pellets were forged at approximately 6200 kg/cm$^2$ (88,000 psi) for approximately 7 seconds at room temperature producing a forged foil having a thickness of 0.1 mm (0.004 mil). The foil exhibited good flexibility and could be bent 90 degrees and back for multiple cycles without breakage. The foil had an area of 0.195 cm$^2$. The silver chloride foil was cathodically discharged by adhering a sheet of an electrically conductive adhesive to one surface of the foil. The adhesive was electrically connected to the negative pole of a galvanostat. The free surface of the foil was placed against a liquid electrolyte gel formulation comprised of 10% hydroxyethylcellulose and 0.1 M NaCl, and the remainder deionized water. A silver foil anode was electrically connected to the positive pole of the galvanostat and placed against the free surface of the gel. Cathode A was cathodically discharged at 0.47 mA/cm$^2$. During discharge, the voltage of Cathode A was measured versus Ag/AgCl quasi-reference electrodes and is plotted in FIG. 3. The foil had a discharge time, as measured by the time it took for the voltage to rise above about 0.5 volts, of 23.5 hours. Furthermore, Cathode A exhibited a volumetric discharge capacity of 1040 mAhr/cm$^3$, utilizing (i.e., by electrochemically reducing) 100% of the silver chloride.

A silver chloride composite film cathode (Cathode B) was tested in an identical manner as described above. Cathode B was composed of 55 vol. % polyisobutylene (PIB) rubber which was a 50:50 mix of a high molecular weight (1.2 million dalton) PIB and a low molecular weight (35 thousand dalton) PIB, 25 vol. % silver chloride particles and 20 vol. % carbon fibers. Cathode B had a thickness of 0.15 mm (i.e., the thickness of Cathode B was 50% more than the thickness of Cathode A) and an area of 2 cm$^2$ (i.e., the area of Cathode B was about 10 times the area of Cathode A). Cathode B was cathodically discharged at 0.3 mA/cm$^2$. During discharge, the voltage of Cathode B was measured versus Ag/AgCl quasi-reference electrodes and is also plotted in FIG. 3. The composite film cathode had a discharge time, as measured by the time it took for the voltage to rise above about 0.5 volts, of only 14.6 hours. Furthermore, Cathode B was tested under more favorable conditions (i.e., thicker, greater area and lower current density) than Cathode A. Even under these more favorable test conditions, the discharge time of Cathode B was still significantly shorter (i.e., less discharge capacity) than the discharge time of Cathode A. Furthermore, because the volume loading of silver chloride in Cathode B was only 25% (as opposed to 100% volume loading for Cathode A), Cathode B exhibited a volumetric discharge capacity of only 260 mAhr/cm$^3$, even though 100% of the silver chloride was electrochemically reduced.

Having thus generally described our invention and described in detail certain preferred embodiments, it will be readily apparent that various modifications to the invention may be made by persons skilled in this art without departing from the scope of this invention and which is limited only by the following claims.

What is claimed is:

1. A method of making a cathodic electrode assembly for an electrotransport device for delivering or sampling an agent through a body surface, the method comprising:

forming a solid silver halide cathodic electrode from silver halide particles, said electrode comprising at least 95 vol. % silver halide, the electrode having an organic material content of less than 1 vol. % and being substantially free of any electrically conductive filler which absorbs cathodic electrolyte reservoir formulation materials; wherein said electrode has a discharge capacity of at least 500 mAhr/cm$^3$; and providing a cathodic electrolyte reservoir wherein said electrolyte reservoir is positioned adjacent to and in ion transmitting relation with the electrode, the electrolyte reservoir while in use being positioned intermediate the electrode and the body surface, and in ion transmitting relation with the body surface.

2. The method of claim 1, wherein the electrode consists essentially of silver halide.

3. The method of claim 1, wherein the silver halide is selected from the group consisting of silver chloride, silver bromide, silver iodide and silver fluoride.

4. The method of claim 1, including contacting the electrode with a current collector, the current collector having an electrical sheet resistance that is less than one-half the sheet resistance of the silver halide electrode.

5. The method of claim 4, wherein the current collector is selected from the group consisting of metal foils, an electrically conductive adhesive, a conductive ink and a conductive coating.

6. The device of claim 1, wherein the electrode further contains up to about 5 vol. % of metallic silver homogeneously dispersed in the electrode.

7. The method of claim 1, wherein the electrode is in the form of a sheet having a thickness of less than 0.5 mm.

8. The method of claim 1, including forging silver chloride particles to form an electrode in the form of a foil.

9. The method of claim 8, wherein the foil is ductile.

10. The method of claim 8, wherein the foil is flexible.

11. The method of claim 8, wherein the foil is non-friable.

12. The method of claim 1, including casting molten silver halide into a sheet and calendering the sheet to form the electrode.

13. The method of claim 1, including forming the electrode by depositing a liquid slurry of silver halide particles onto a screen, drawing off the liquid to form a silver halide sheet and calendering the sheet.

14. The method of claim 1, including mixing silver halide particles in an organic binder, forming a sheet of the silver halide-loaded binder and pyrolyzing the sheet to substantially burn off the binder in order to form the foil.

15. The method of claim 1, wherein the silver halide is silver chloride.

\* \* \* \* \*